United States Patent [19]

Markovac et al.

[11] Patent Number: 5,917,040
[45] Date of Patent: Jun. 29, 1999

[54] 2-FLUORO-9-TRIMETHYLSILYLADENINE

[75] Inventors: Anica Markovac, Lathrup Village; Maurice P. LaMontagne, Farmington Hills, both of Mich.

[73] Assignee: Ash Stevens, Inc., Detroit, Mich.

[21] Appl. No.: 08/063,652

[22] Filed: May 20, 1993

Related U.S. Application Data

[62] Division of application No. 07/910,498, Jul. 8, 1992, abandoned.

[51] Int. Cl.⁶ .................. C07D 473/00; C07D 473/40
[52] U.S. Cl. ........................... 544/264; 544/267
[58] Field of Search ...................... 544/264, 267

[56] References Cited

U.S. PATENT DOCUMENTS

| | | | |
|---|---|---|---|
| 3,748,320 | 7/1973 | Vorbruggen et al. | 536/28.3 |
| 4,082,911 | 4/1978 | Vorbruggen | 536/27.11 |
| 4,188,378 | 2/1980 | Montgomery | 514/46 |
| 4,209,613 | 6/1980 | Vorbruggen | 536/27.11 |
| 4,210,745 | 7/1980 | Montgomery | 536/27.7 |
| 4,323,573 | 4/1982 | Schaeffer et al. | 424/253 |
| 4,357,324 | 11/1982 | Montgomery et al. | 514/46 |
| 4,760,137 | 7/1988 | Robins et al. | 536/27.11 |
| 5,110,919 | 5/1992 | Blumbergs et al. | 536/27.4 |
| 5,206,351 | 4/1993 | Markovac et al. | 536/27.11 |

OTHER PUBLICATIONS

Montgomery et al., J. Med. Chem. 12, 498–504 (1969).
Montgomery et al., J. Het. Chem. 16, 157–160 (1979).
Eaton et al. J. Org. Chem. 34(3):747–748, 1969.
Keller et al. J. Org. Chem. 32: 1644–1646, 1967.
White et al. J. Org. Chem. 37(3): 430–438, 1972.

*Primary Examiner*—Gary L. Kunz
*Attorney, Agent, or Firm*—Ian C. McLeod

[57] ABSTRACT

A process for the preparation of 2-fluoro-9- (2,3,5-tri-O-benzyl-beta-D-arabinofuranosyl)adenine (I) is described. The process involves reacting a protected 2-fluoro adenine with a protected chlorosugar under controlled conditions of temperature (80–85° C.) to produce (I), rather than using a process involving fluorinating a 2-substituted nucleoside precursor of (I).

1 Claim, No Drawings

2-FLUORO-9-TRIMETHYLSILYLADENINE

This is a divisional of application Ser. No. 07/910,498 filed on Jul. 8, 1992 now abandoned.

BACKGROUND OF THE INVENTION (1) Field of The Invention

The present invention relates to an improved process for the preparation of 2-fluoro-9-(2,3,5-tri-O-benzyl-beta-D-arabinofuranosyl) adenine (I). In particular the present invention relates to a process wherein a protected fluoroadenine is reacted with a protected chlorosugar to improve the yields and reduce the cost of the desired compound (I).

(2) Prior Art

U.S. Pat. Nos. 4,188,378; 4,210,745 and 4,357,324 to Montgomery or Montgomery and Shortnacy, Montgomery et al, J. Med. Chem. 12, 498–504 (1969) and J. Het. Chem. 16, 157–160 (1979) describe various procedures for the preparation of 2-substituted-9-(2,3,5-tri-O-benzyl-beta-D-arabinofuranosyl) adenine compounds wherein the 2-substituent can be converted to a fluoro group. The problem is that the fluorination step in the 2-position is difficult and produces low yields. Since the cost of the protected sugar is high, the low yield (≈37%) of the 2-fluoronucleoside significantly impacts the cost of the final product which is 9-beta-D-arabinofuranosyl-2-fluoroadenine or the 5'phosphate.

OBJECTS

It is therefore an object of the present invention to provide a process for the preparation of 2-fluoro-9-(2,3,5-tri-O-benzyl-beta-D-arabinofuranosyl) adenine (I) which eliminates the need to convert a 2-substituted intermediate to a 2-fluoroadenine. Further, it is an object of the present invention to provide a process for producing fluoroadenine (I) in good yields. These and other objects will become increasingly apparent by reference to the following description.

GENERAL DESCRIPTION

The present invention relates to a process for the preparation of 2-fluoro-9-(2,3,5-tri-O-benzyl-beta-arabinofuranosyl)adenine (I) which comprises:

(a) reacting in a first reaction mixture a compound (II) of the formula:

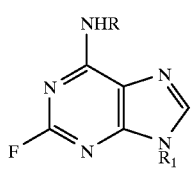

where R is selected from the group consisting of hydrogen, trimethylsilyl and methoxyacetyl and $R_1$ is selected from the group consisting of hydrogen and trimethylsilyl with a compound (III)

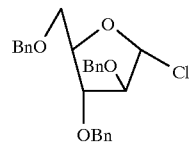

wherein Bn is benzyl in a solvent for (II) and (III) with heating at a temperature between about 80 and 85° C., with an acid acceptor when R is methoxyacetyl to produce compound (IV)

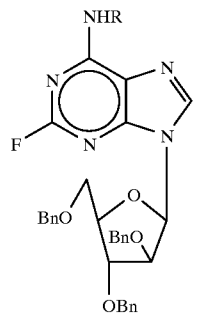

(b) reacting the reaction mixture containing compound (IV) with a lower alkanol and an acid acceptor (preferably triethylamine) where R is trimethylsilyl or hydrogen and with sodium methoxide and then an acid when R is methoxyacetyl to provide (I) in the resulting reaction mixture; and (c) separating (I) from the resulting reaction mixture.

Preferably the acid acceptor is a Lewis base such as a lower (mono-, di- or tri-) alkylamine (1 to 6 carbon atoms), preferably diisopropylamine or other di-lower alkylamines. Various resins with acid accepting properties can be used as is well known to those skilled in the art.

A lower alkanol is used in step (b). The lower alkanol can contain 1 to 3 carbon atoms. Methanol is preferred.

In particular the present invention relates to a process for the preparation of 2-fluoro-9-(2,3,5-tri-O-benzyl-beta-arabinofuranosyl)adenine(I) which comprises:

(a) reacting in a reaction mixture a compound (II) of the formula:

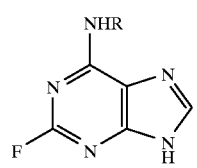

wherein R is methoxyacetyl with a compound (III)

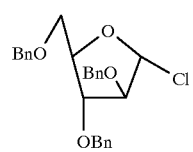

wherein Bn is benzyl in a solvent for (II) and (III) with heating at a temperature between about 80 and 85° C., in the presence of a Lewis base as an acid acceptor, to produce an intermediate (IV)

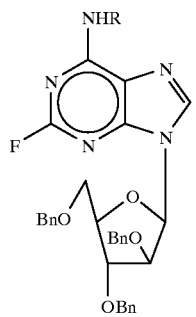

in the reaction mixture;

(b) removing the methoxyacetyl R group from the intermediate (IV) to produce (I) by a reaction of intermediate (IV) with sodium methoxide and then an acid in a second solvent; and (c) separating (I) from the reaction mixture.

Finally the present invention relates to a process for the preparation of 2-fluoro-9-(2,3,5-tri-O-benzyl-beta-arabinofuranosyl)adenine (I) which comprises:

(a) reacting in a reaction mixture a compound (II) of the formula:

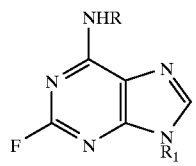

where R is selected from the group consisting of hydrogen and trimethylsilyl and $R_1$ is trimethylsilyl with a compound (III)

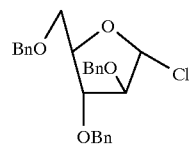

wherein Bn is benzyl in a solvent for (II) and (III) with heating at a temperature between about 80 and 85° C., to produce compound (IV)

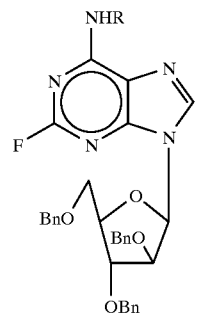

(b) reacting the mixture containing compound (IV) with a lower alkanol in the presence of an acid acceptor (triethylamine); and (c) separating (I) from the reaction mixture.

SPECIFIC DESCRIPTION

The following reaction sequence show the preparation of 2-fluoro-9-(2,3,5-tri-O-benzyl-β-arabinofuranosyl)adenine (I)

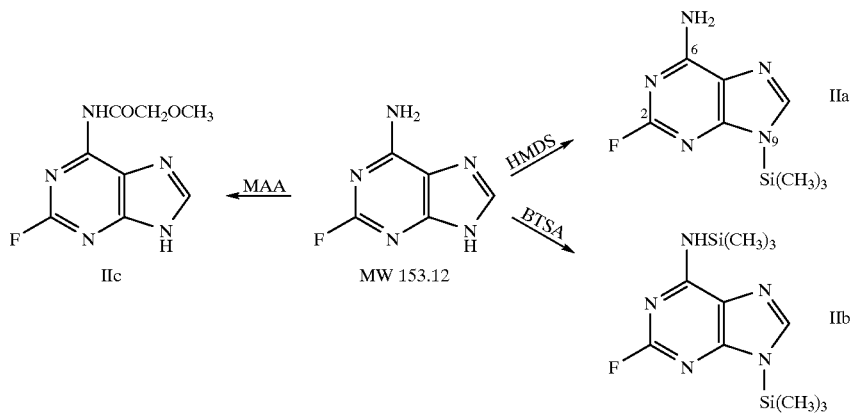

MAA = Methoxyacetic anhydride
HMDS = Hexamethyldisilazane
BTSA = Bis(trimethylsilyl) acetamide

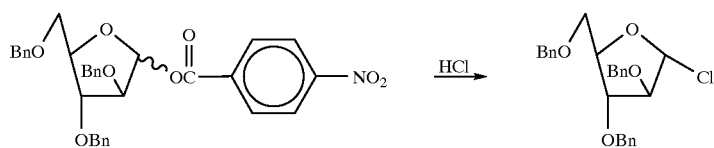

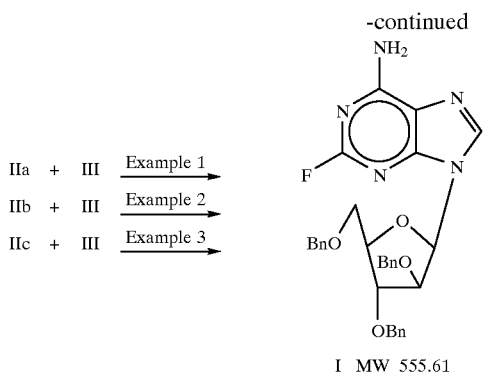

I MW 555.61

The following Examples show the preparation of fluoroadenine (I) by a coupling reaction and the starting compounds.

I. Starting Compounds

2-Fluoro-9-trimethylsilyladenine (IIa)

A stirred suspension of 2-fluoroadenine (5.0 g, 0.033 mol) prepared by the process of Eaton et al, J. Organic Chem 34 747 (1969) and powdered ammonium sulfate (0.5 g) in hexamethyldisilazane (HMDS, 500 mL) was heated to reflux. The reaction mixture was concentrated by distillation to a smaller volume (300 mL) and was then diluted with additional HMDS (200 mL). The mixture was refluxed overnight and was then concentrated by distillation at atmospheric pressure to a smaller volume (150 mL). Residual HMDS was removed by distillation in vacuo (aspirator) followed by drying at room temperature/0.05 mmHg to give 7.8 g (ca. 100%) of the title intermediate IIa as a crystalline solid.

2-Fluoro-bis(6,9-trimethylsilyl)adenine (IIb)

A suspension containing 2-fluoroadenine (3.06 g, 0.02, mol) and bis(trimethylsilyl)acetamide (BTSA, 12.2 g, 0.06 mol, 14.8 mL) in acetonitrile (15 mL) was refluxed with stirring for 30 minutes. Additional BTSA (2.4 mL, 0.01 mol) was added and the mixture refluxed for another 30 minutes (total 1 hour) to form a clear yellow solution. Solvent and the excess of BTSA were removed (aspirator) and the residue dried (0.1 mmHg, 20–25° C.) to afford the protected 2-fluoroadenine IIb which was used as such in the next step.

2-Fluoro-6-methoxyacetyladenine (IIc)

2-Fluoroadenine (1 g, ca. 95% pure) was added with stirring to boiling (heating mantle) methoxyacetic anhydride (MAA, 15 mL). A clear solution was obtained. The heating mantle was removed immediately, the hot solution was stirred for an additional 5 minutes and evaporated to dryness (vacuum pump). The residual product was dissolved in methanol (10 mL) to destroy the remaining MAA, and the reaction mixture evaporated to dryness (aspirator). The crude product was dissolved in THF (10 mL), the solution diluted with $CH_2Cl_2$ (50 mL) and carefully neutralized using 10% aq. sodium bicarbonate. The aqueous layer was separated and extracted with more $CH_2Cl_2$ (2×50 mL). The organic layers were combined, dried ($MgSO_4$), charcoaled and the solvent evaporated (aspirator) to yield the crude product Ic. This was dissolved in hot aq. THF (95% THF: 5% water, 10 mL), and the cloudy solution was filtered (celite) and refrigerated for several hours. Crystalline amide IIc was separated, washed with a mixture of THF and $Et_2O$ (1:1, 5 mL) and dried to give the product IIc, 850 mg, mp 221–223° C. Rework of the mother liquor afforded the second crop, 100 mg, mp 221–223° C. Total yield was 950 mg (68%).

Anal. Calcd for $C_8H_8FN_5O_2$ (225.2): C, 42.67; H, 3.58; F, 8.44; N, 31.10. Found: C, 42.60; H, 3.39; F, 8.53; N, 30.91.

1-Chloro-2,3,5-tri-O-benzyl-α-D-arabinose (III)

Hydrogen chloride gas was bubbled into a stirred solution of 2,3,5-tri-O-benzyl-1-O-p-nitrobenzoyl-D-arabinose (19.5 g, 0.034 mol) in methylene chloride (150 mL) at 0–5° C. for 1 hour. The reaction mixture was warmed to 20° C., purged with nitrogen for 10 minutes, and filtered through sintered glass. The filtrate was concentrated (aspirator) to a syrup. The syrup was dissolved in ethylene dichloride (50 mL) and the solution was concentrated (aspirator) and dried at room temperature/0.05 mmHg for 1 hour to give 15.8 g (ca. 100%) of the title intermediate 2 as a syrup.

EXAMPLE 1

2-Fluoro-9-(2 3.5-tri-O-benzyl-β-D-arabinofuranosvl)adenine (I)

A solution of 1-chloro-α-D-arabinose (III) (15.8 g, 0.036 mol) in dichloroethane (EDC, 300 mL) was added to 2-fluoro-9-trimethylsilyladenine (IIa, 7.8 g, 0.035 mol) and the mixture was heated with stirring to ref lux. Portions (10×50 mL) of the dichloroethane were removed by distillation while maintaining the original volume of the reaction mixture by the addition of an equal volume of fresh dichloroethane. The mixture was refluxed overnight and was then concentrated to a smaller volume (150 mL), and cooled to 10° C. The mixture was treated with triethylamine (5.0 mL) to pH 9, followed by the addition of methanol (50 mL) and was heated to reflux for 10 minutes. The mixture was cooled to room temperature and filtered. The filtrate was concentrated to a syrup. The syrup was dissolved in ethyl acetate (300 mL). The solution was washed with saturated aqueous sodium chloride (2×50 mL). The organic layer was dried ($MgSO_4$), treated with charcoal (5 g) and filtered (celite). The filtrate was concentrated to a wet solid. The solid was triturated with ether (100 mL) and was removed by filtration, washed with ether (50 mL) and air dried overnight to give 8.7 g (48%) of crude title product as a brown crystalline solid. The crude product (I) was dissolved in boiling ethyl acetate (100 mL) and the solution was treated with charcoal (1 g) and filtered (celite). The filtrate was diluted with ether (200 mL) and the mixture was allowed to sit at room temperature overnight. The solid was collected and washed with ether (50 mL) and dried at room temperature/0.05 mmHg to give 7.1 g (39%) of product (I) as a crystalline solid, mp 158–160° C. (Melting point corresponds to authentic melting point which was run simultaneously; mixed melting point is undepressed). $[\alpha]_D$+17.6°, (c=0.93, CHCl$_3$).

EXAMPLE 2

A solution of the chlorosugar III prepared as above from 11.4 g, 0.02 mol of protected arabinose in EDC (80 mL) was added to a solution of IIb (prepared from 3.06 g, 0.02 mol of 2-fluoro-adenine) in EDC (20 mL) and the mixture was heated with stirring at reflux. Portions of the dichloroethane (2×50 mL) were removed by distillation while maintaining the original volume by the addition of an equivalent amount of fresh dichloroethane. The mixture was heated at reflux overnight and was then concentrated to a smaller volume (50 mL) and cooled to 10° C. The mixture was treated with triethylamine (5 mL) to pH 9, followed by the addition of methanol (50 mL). The mixture was heated at reflux for 10 minutes. The mixture was cooled to room temperature and filtered (Celite). The filtrate was concentrated (aspirator) to a syrup. The syrup was dissolved in ethyl acetate (300 mL) The solution was washed with water, dried (MgSO$_4$), treated with charcoal, and filtered (Celite). The solvent was evaporated and the residue was dissolved in ethyl acetate (50 mL). The cleaar solution was diluted with diethyl ether (50 mL). After seeding and cooling to ≈50° C. the crystalline product was filtered, washed with ether and air dried to afford pure I, 5.4 g, 52%. This material was identical in all respects with the authentic sample of product (I), mp 158–160° C. [α]+17.9 (c=1, CHCl$_3$); elemental analysis (C, H, F, N) acceptable.

EXAMPLE 3

A reaction mixture containing the chlorosugar III (prepared as above from 569 mg, 0.001 mol of the protected arabinose), amide IIc (225 mg, 0.001 mol) and diisopropylamine (129 mg, 0.001 mol) in EDC (30 mL) was heated to reflux while a portion of EDC (ca. 10 mL) was distilled off. The mixture was refluxed for ca. 22 hours, and poured in water (100 mL). The organic layer was separated, and the aqueous portion was extracted with EDC (2×20 mL). The organic layers were combined, washed with water, dried (MgSO$_4$), and evaporated to dryness (aspirator). The syrupy residue (6-methoxyacetyl protected (I) was dissolved in methanol (15 mL). Sodium methoxide (100 mg) was added, and the solution was stirred at room temperature for ca. 3 hours (deprotection completed by TLC analysis). Acetic acid (10% aq. solution) was added (pH 7) and the suspension evaporated to dryness. The crude product (I) was dissolved in CH$_2$Cl$_2$ (10 mL), the solution was washed with water, dried (MgSo$_4$), concentrated (aspirator), and the residue (ca. 400 mg) was crystallized twice from a mixture of ethyl acetate (2 mL) and ether (3 mL). Pure (I) was obtained, 240 mg (44%), identical in all respects with the authentic sample, mp 158–160° C.; ([α]+17.8° (c=1, CHCl$_3$). Elemental analysis (C,H,F,N) acceptable.

It is intended that the foregoing description be only illustrative of the present invention and that the present invention be limited only by the hereinafter appended claims.

We claim:

1. 2-Fluoro-9-trimethylsilyladenine.

* * * * *